(12) United States Patent
Guidry et al.

(10) Patent No.: US 7,273,939 B1
(45) Date of Patent: Sep. 25, 2007

(54) METHODS OF MAKING TRIS(N-ARYL BENZIMIDAZOLES)BENZENES AND THEIR USE IN ELECTRONIC DEVICES

(75) Inventors: Mark A. Guidry, New Castle, DE (US); Steven W. Shuey, Landenberg, PA (US); William J. Delaney, Bear, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/305,480

(22) Filed: Dec. 15, 2005

Related U.S. Application Data

(60) Provisional application No. 60/694,920, filed on Jun. 28, 2005, provisional application No. 60/694,901, filed on Jun. 28, 2005, provisional application No. 60/640,262, filed on Dec. 30, 2004, provisional application No. 60/639,057, filed on Dec. 22, 2004.

(51) Int. Cl.
C07D 403/10 (2006.01)

(52) U.S. Cl. .................................................. 548/310.7

(58) Field of Classification Search ............ 548/310.7
See application file for complete search history.

(56) References Cited

U.S. PATENT DOCUMENTS

| | | | | |
|---|---|---|---|---|
| 5,645,948 | A | 7/1997 | Shi et al. | 428/690 |
| 5,766,779 | A | 6/1998 | Shi et al. | 428/690 |
| 6,171,715 | B1 | 1/2001 | Sato et al. | 428/690 |
| 6,303,238 | B1 | 10/2001 | Thompson et al. | 428/690 |
| 6,436,558 | B1 | 8/2002 | Sato et al. | 428/690 |
| 6,461,747 | B1 | 10/2002 | Okada et al. | 428/690 |
| 2001/0019782 | A1 | 9/2001 | Igarashi et al. | 428/690 |
| 2002/0037427 | A1* | 3/2002 | Taguchi | 428/690 |

FOREIGN PATENT DOCUMENTS

| | | |
|---|---|---|
| EP | 1 191 612 A2 | 3/2002 |
| EP | 1 191 614 A2 | 3/2002 |
| WO | WO 00/70655 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

U.S. Appl. No. 11/305,488, filed Dec. 15, 2005, Shuey et al.
Campbell, I.H. et al., "Excitation Transfer Processes in a Phosphor-Doped Poly (*p*-phenylene vinylene) Light-Emitting Diode", *Physical Review B.*, vol. 65, 085210-1-085210-8, 2002.
Forrest, S.R., "The Path to Ubiquitous and Low-Cost Organic Electronic Appliances on Plastic", *Nature*, 2004, 428, 911-918.
Gustafsson, G. et al., "Flexible Light-Emitting Diodes made from Soluble Conducting Polymer", *Nature*, 1992, 357, 477-479.
O'Brien, D.F. et al., "Electrophosphoresence from a Doped Polymer Light Emitting Diode", *Synthesis Metals*, 2001, 116(1-3), 379-383.
Othmer, K., *Encyclopedia of Chemical Technology*, 1996, 18 (4th Ed), 837-860.

* cited by examiner

*Primary Examiner*—Laura L. Stockton
(74) *Attorney, Agent, or Firm*—Woodcock Washburn LLP

(57) ABSTRACT

Provided are methods for preparing a compound of Formula I:

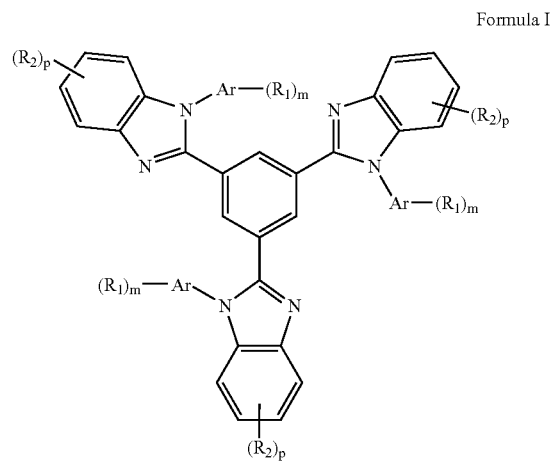

Formula I where the method comprises the steps of:
contacting a compound of Formula II:

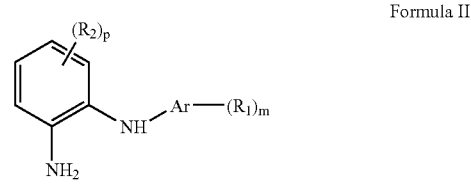

Formula II with 1,3,5-benzene-tricarbonyl chloride in the presence of a polar aprotic solvent to form an amide adduct; and subsequently condensing the amide with a proximate anilino group present in the adduct in the presence of a condensing agent to form a compound of Formula I wherein $R_1$, $R_2$, Ar, m, p, and t are as defined in the specification.

10 Claims, 1 Drawing Sheet

METHODS OF MAKING TRIS(N-ARYL BENZIMIDAZOLES)BENZENES AND THEIR USE IN ELECTRONIC DEVICES

CROSS-REFERENCE TO RELATED APPLICATIONS

This application claims benefit to U.S. Provisional Application Ser. Nos. 60/639,057, filed Dec. 22, 2004; 60/694,920, filed Jun. 28, 2005; 60/640,262, filed Dec. 30, 2004; and 60/694,901 filed Jun. 28, 2005, each of which are incorporated herein by reference in their entireties.

FIELD

This disclosure relates generally to methods of preparing tris(N-aryl-benzimidazole) benzenes, and their use in electronic devices, for example, and methods for fabrication of the same.

BACKGROUND

Organic electronic devices convert electrical energy into radiation, detect signals through electronic processes, convert radiation into electrical energy, or include one or more organic semiconductor layers. Most organic electronic devices include a conductive layer (such as a light-emitting or photoactive layer) positioned between two electrodes. In some devices, a charge transport layer can be utilized between the conductive layer and an electrode. For example, a hole transport layer can be positioned between the conductive layer and the anode and a electron transport layer can be positioned between the conductive layer and the cathode.

Thus, what is needed are additional materials for use in organic electronic devices.

SUMMARY

In one embodiment, methods of preparing tris(N-aryl-benzimidazole)benzene compounds having Formula I:

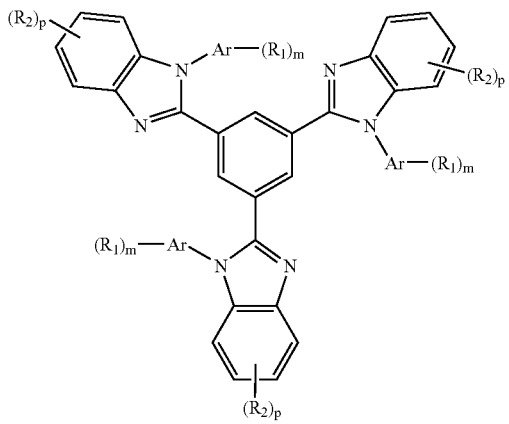

Formula I wherein:

R$_1$ is the same or different at each occurrence and is hydrogen, C$_1$-C$_{20}$ alkyl, halo, C$_1$-C$_{20}$ fluoroalkyl, C$_6$-C$_{20}$ aryl, C$_4$-C$_{20}$ heteroaryl, C$_1$-C$_{20}$ alkoxy, C$_6$-C$_{20}$ aryloxy, C$_1$-C$_{20}$ thioalkoxy, C$_6$-C$_{20}$ thioaryloxy, amino, carboxyl, cyano, nitro, or two adjacent R groups together can be —O—(CH$_2$)$_t$—O— or a fused aromatic ring;

R$_2$ is the same or different at each occurrence and is hydrogen, C$_1$-C$_{20}$ alkyl, halo, C$_1$-C$_{20}$ fluoroalkyl, C$_6$-C$_{20}$ aryl, C$_4$-C$_{20}$ heteroaryl, C$_1$-C$_{20}$ alkoxy, C$_6$-C$_{20}$ aryloxy, C$_1$-C$_{20}$ thioalkoxy, C$_6$-C$_{20}$ thioaryloxy, amino, carboxyl, cyano, nitro, or two adjacent R groups together can be —O—(CH$_2$)$_t$—O— or a fused aromatic ring;

Ar is the same or different at each occurrence and is C$_6$-C$_{20}$ aryl or C$_4$-C$_{20}$ heteroaryl;

m, and p are the same or different at each occurrence and are each independently 0 or an integer from 1 to 3 wherein m and p in each occurrence can be the same or different; and t is the same or different at each occurrence and is an integer from 1 to 6;

where the method comprises the steps of:

contacting a compound of Formula II:

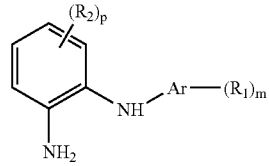

Formula II with 1,3,5-benzene-tricarbonyl chloride in the presence of a polar aprotic solvent to form an amide adduct; and subsequently condensing the amide with a proximate anilino group present in the adduct in the presence of a condensing agent to form a compound of Formula I, are provided, as well as devices and sub-assemblies including the same.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
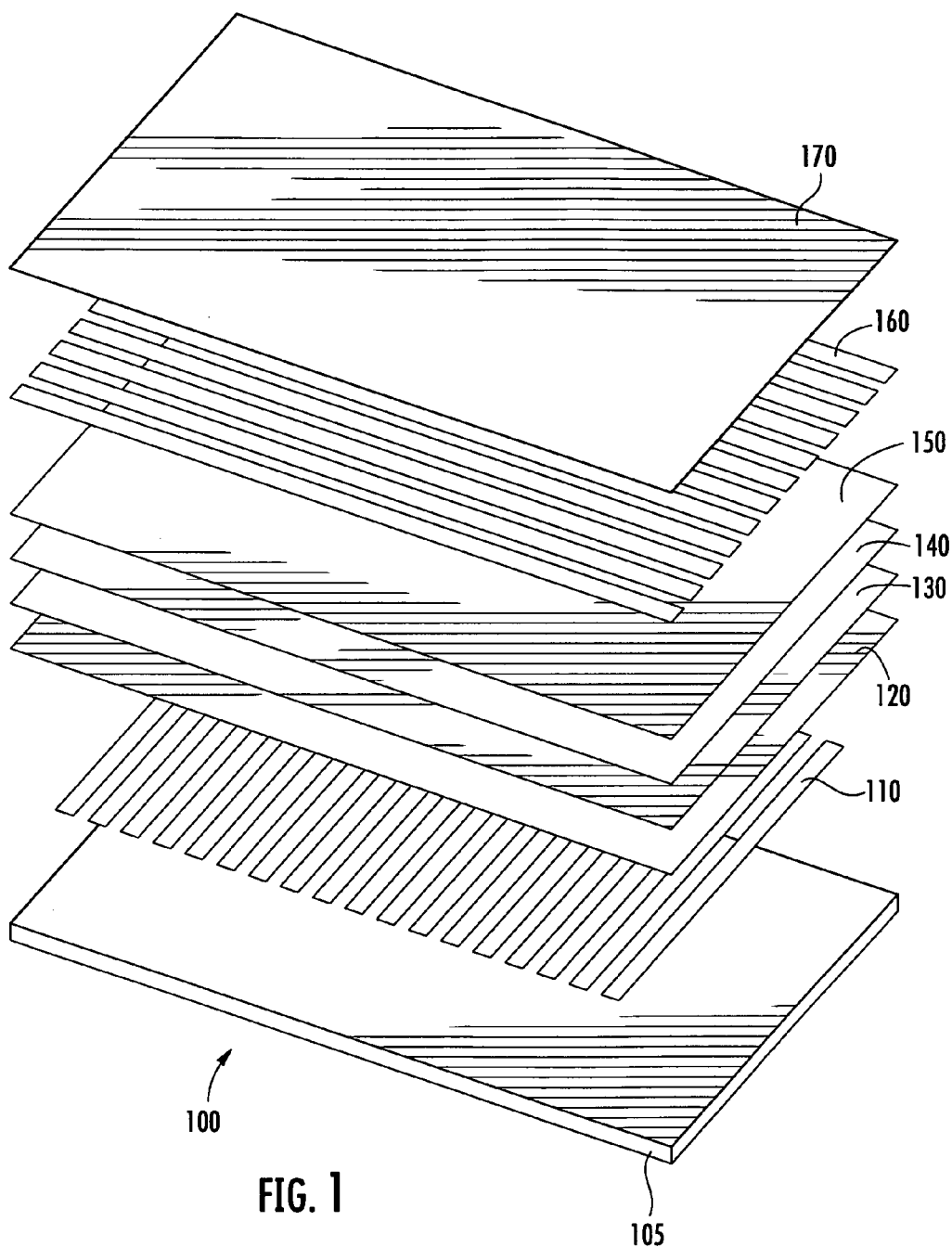
FIG. 1 includes an illustration of an exemplary organic electronic device that may include one layer comprising a compound made according to the methods disclosed herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

In one embodiment, provided are methods for preparing a compound of Formula I:

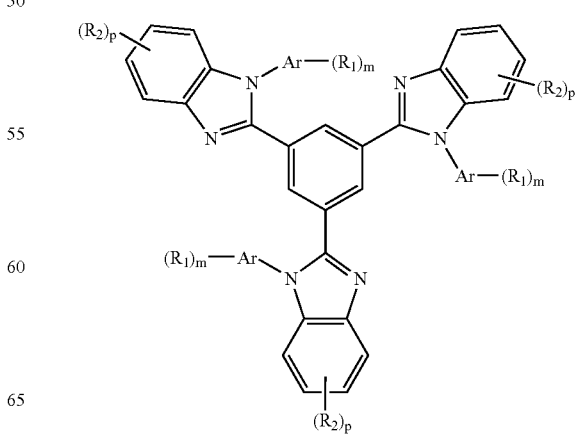

Formula I where the method comprises the steps of:
contacting a compound of Formula II:

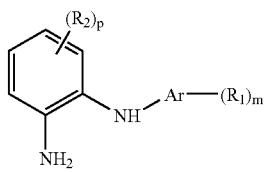

Formula II with 1,3,5-benzene-tricarbonyl chloride in the presence of a polar aprotic solvent to form an amide adduct; and subsequently condensing the amide with a proximate anilino group present in the adduct in the presence of a condensing agent to form a compound of Formula I. wherein:

$R_1$ is the same or different at each occurrence and is hydrogen, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

$R_2$ is the same or different at each occurrence and is hydrogen, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

Ar is the same or different at each occurrence and is $C_6$-$C_{20}$ aryl or $C_4$-$C_{20}$ heteroaryl;

m, and p are the same or different at each occurrence and are each independently 0 or an integer from 1 to 3; and t is the same or different at each occurrence and is an integer from 1 to 6.

Generally, the methods comprise the steps of contacting 1 equivalent of 1,3,5-benzene-tricarbonyl chloride with at least 3 equivalents of a compound of Formula II in the presence of a polar aprotic solvent to form the amide adduct. The substituent groups for each equivalent of a compound of Formula II can be the same or different.

In one embodiment, 2,2',2"-(1,3,5-phenylene)-tris[1-phenyl-1H-benzimidazole] is prepared by contacting N-phenyl-1,2-phenylenediamine with 1,3,5-benzene-tricarbonyl chloride in the presence of a polar aprotic solvent.

Suitable condensing agents include $POCl_3$, diphenyl chlorophosphate, phosgene, and combinations thereof. The skilled practitioner will appreciate that additional condensing agents capable of condensing the amide adduct with a proximate anilino group present in the adduct to form a compound of Formula I can be used in the present methods. While not wishing to be bound by any particular theory, the condensing agent is believed to activate the amide bond to nucleophilic attack by the intramolecular diarylamine.

In one embodiment, the compound of Formula II is contacted with 1,3,5-benzene-tricarbonyl chloride in the presence of a polar aprotic solvent. In one embodiment, the contacting is performed at a temperature of about 50° C. for about 24 hours.

Suitable polar aprotic solvents include N-Methyl-2-Pyrrolidone (NMP); dimethylformamide (DMF); dimethylacetamide (DMAC); dioxane, tetrahydrofuran (THF); dimethyl sulfoxide (DMSO); toluene; dichlorobenzene; dichloromethane; dichloroethane; and combinations thereof.

In one embodiment of the present methods, the amide adduct is further heated For example, in one embodiment, the step of condensing the amide with a proximate anilino group present in the adduct in the presence of a condensing agent is performed at temperature of from about 25° C. to about 150° C. for about 1 to about 25 hours. In one embodiment, the step of condensing the amide with a proximate anilino group present in the adduct in the presence of a condensing agent is performed at temperature about 98° C. for about 14 hours.

In one embodiment of the present methods, a compound of Formula II is contacted with 1,3,5-benzene-tricarbonyl chloride in the presence of a polar aprotic solvent and further heated. For example, in one embodiment, the step of contacting a compound of Formula II with 1,3,5-benzene-tricarbonyl chloride in the presence of a polar aprotic solvent is performed at a temperature of about 50° C. for about 24 hours.

In one embodiment, the methods further comprise the step of isolating the adduct before contact with the condensing agent. As used herein, "isolation" or the step of "isolating" refers to techniques for separating components in a mixture that have different solubilities in different solvents. Isolation techniques can be used to purify or concentrate components of a mixture. Isolation techniques are well known and may be found, for example, in P. W. Smith, B. S. Furniss, and A. I. Vogel, Vogel's Textbook of Practical Organic Chemistry (5th Edition), (Prentice Hall 1996) and W. L. F. Armarego and C. Chai, Purification of Laboratory Chemicals (5th Edition), (Butterworth-Heinemann 2003), the entire contents of both books are incorporated herein by reference. Any method of isolation can be used in the present invention. For example, in one embodiment, isolation is by filtration. In an exemplary embodiment, the adduct is isolated by cooling to room temperature, precipitating into $NaHCO_3$, and washing with water.

In one embodiment, the method further comprise the step of isolating the compound of Formula I. Any method of isolation can be used in the present invention. In one embodiment, the compound is isolated by cooling to room temperature, precipitating the compound into ice water, neutralizing with a strong base, and collecting the compound by filtration. In one embodiment, the strong base is NaOH. In one embodiment, the neutralized solution has a pH of about 9.

In one embodiment, methods of the present invention comprise the steps of contacting a compound of Formula II:

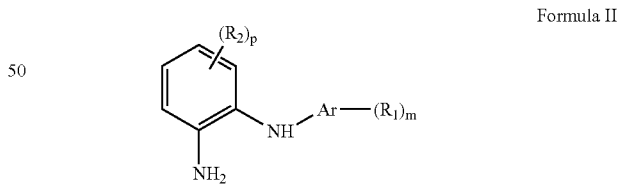

Formula II with 1,3,5-benzene-tricarbonyl chloride in the presence of a polar aprotic solvent to produce a solid; contacting the solid with $POCl_3$ and heating; cooling and precipitating into ice/water; neutralizing with a strong base, and dissolving in a polar solvent, such as, for example, dichloromethane. In one embodiment, 2,2',2"-(1,3,5-phenylene)-tris[1-phenyl-1H-benzimidazole] is prepared by contacting N-phenyl-1,2-phenylenediamine with 1,3,5-benzene-tricarbonyl chloride in the presence of a polar aprotic solvent.

A representative synthetic scheme of the present invention is provided below as Scheme I. Scheme 1 demonstrates exemplary processes for the preparation of 2,2',2"-(1,3,5-phenylene)-tris[1-phenyl-1H-benzimidazole]. The skilled practitioner will know how to make use of variants of these process steps.

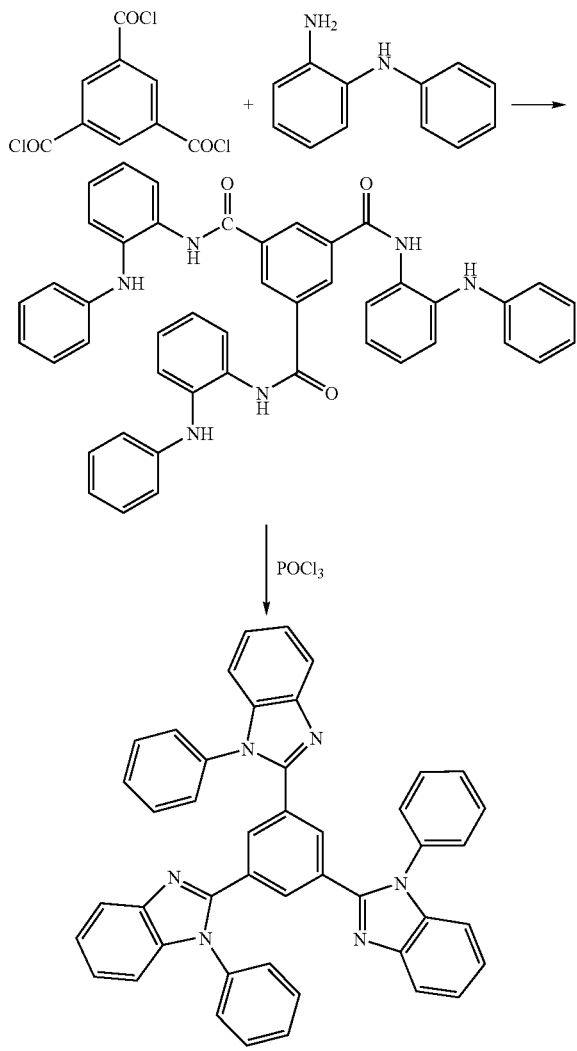

In one embodiment, provided is a composition comprising 2,2',2"-(1,3,5-Phenylene)-tris[1-phenyl-1H-benzimidazole] prepared by the methods herein described. In one embodiment, an organic electronic device comprising 2,2',2"-(1,3,5-phenylene)-tris[1-phenyl-1H-benzimidazole] prepared by the methods herein described is provided.

In one embodiment, a composition comprising 2,2',2"-(1,3,5-phenylene)-tris[1-phenyl-1H-benzimidazole] prepared by the methods herein described, and at least one solvent, processing aid, charge transporting material, or charge blocking material is provided.

One embodiment concerns a compound made by a method described herein as a component of a layer in a single-layer or multi-layer device.

In a further embodiment, the layer can be used as a charge transport layer in a single-layer or multi-layer device. In one embodiment, the charge transport layer is a hole-transport layer. In another embodiment, the charge transport layer is an electron transport layer.

In one embodiment, the compound of Formula I is 2,2',2"-(1,3,5-phenylene)-tris[1-phenyl-1H-benzimidazole].

In one embodiment, when Ar is phenyl, at least one of $R^2$, $R^4$ and $R^6$ is $C_1$-$C_{20}$ alkyl, halo, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O—. In yet other embodiments, when Ar is phenyl, at least one of $R^1$, $R^3$ and $R^5$ is $C_1$-$C_{20}$ alkyl, halo, $C_1$-$C_{20}$ fluoroalkyl, $C_6$-$C_{20}$ aryl, $C_4$-$C_{20}$ heteroaryl, or two adjacent R groups together can be —O—$(CH_2)_t$—O—.

In one embodiment, Ar is phenyl, naphthyl, or pyridinyl.

In one embodiment, $R^1$-$R^6$, are each, independently, H, F, $CF_3$, phenyl, $C_1$-$C_6$ alkyl, or two adjacent R groups can be —O—$CH_2$—O— or a fused aromatic ring.

In one embodiment, $R^1$, $R^2$ and $R^3$ are H. $R^4$, $R^5$, and $R^6$ can each be H in some compounds In one embodiment, $R^4$, $R^5$ and $R^6$ are each independently H, $C_1$-$C_6$ alkyl, F, $CF_3$ or phenyl.

Certain tris(N-aryl-benzimidazole)benzene compounds are such that m, n, p, q, r, and s are each independently 0 or 1.

Exemplary tris(N-aryl-benzimidazole)benzene compounds are 2,2',2"-(1,3,5-phenylene)-tris[1-phenyl-1H-benzimidazole],

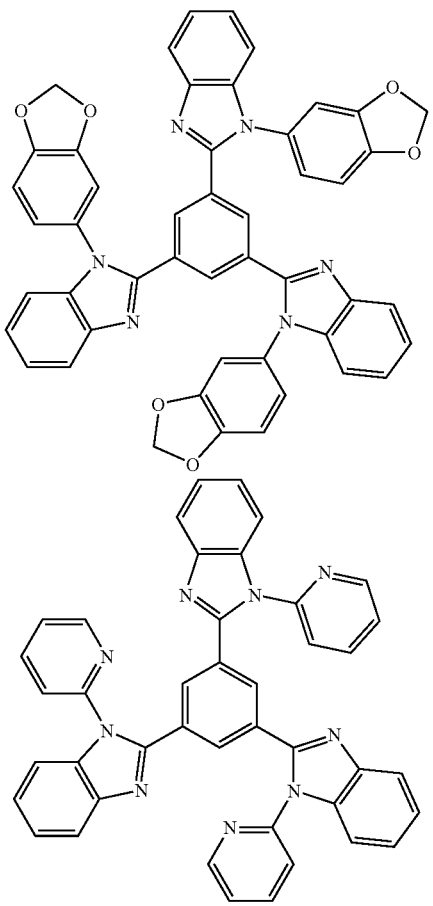

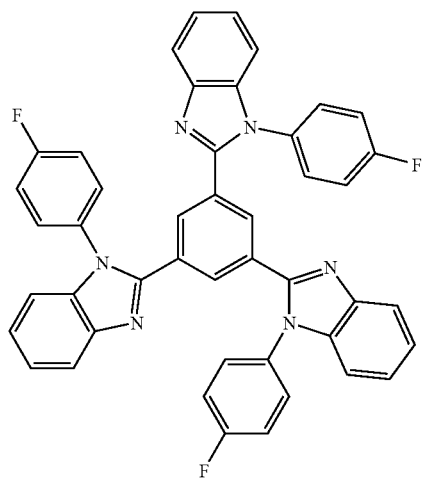
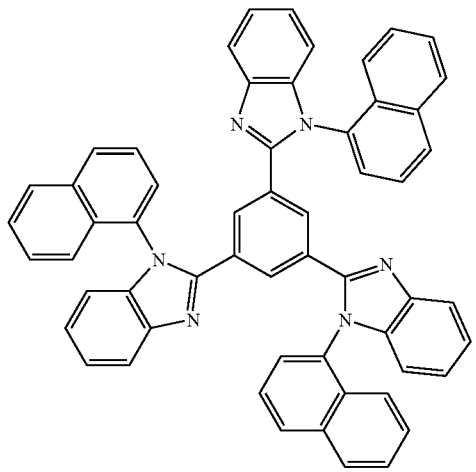
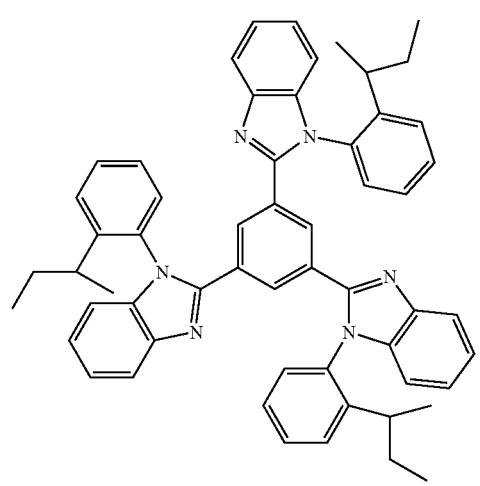
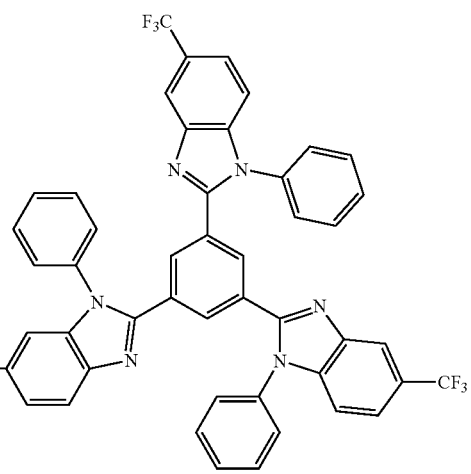
and
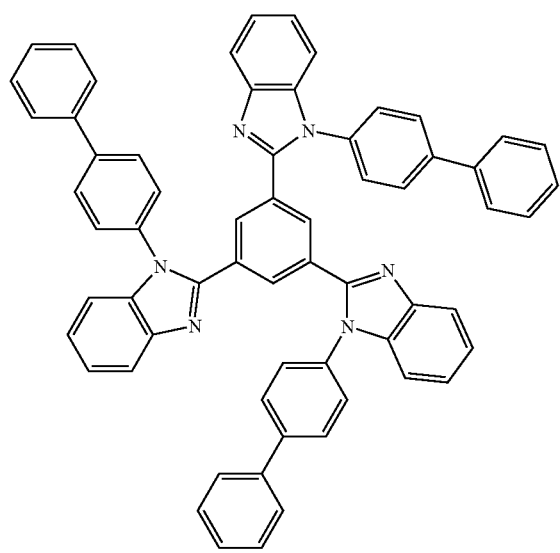
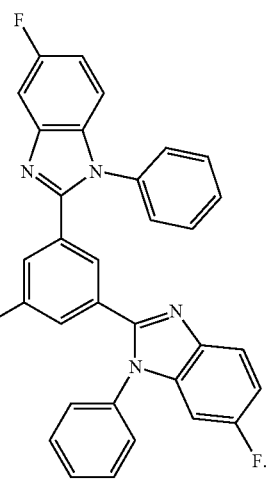
In one embodiment, compositions comprising at least one of the above described tris(N-aryl-benzimidazole)benzene compounds can be admixed with a polymer. In other embodiments, the composition may be a solution, dispersion, emulsion, or a colloid and may contain one or more solvents as processing aids.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one embodiment, the tris(N-aryl-benzimidazole)benzene compounds have charge transport properties.

In one embodiment, the tris(N-aryl-benzimidazole)benzene compounds have a glass transition temperature ("$T_g$") that is higher than the tris(N-aryl-benzimidazole)benzene compounds without $R^1$-$R^6$ substituents. In one embodiment, the compounds with higher $T_g$ form better films when deposited by either vapor or solution processing methods. In one embodiment, the $T_g$ is greater than 125° C. In another embodiment, the $T_g$ is greater than 130° C.

In one embodiment, provided is an electronic device containing at least one layer having at least one tris(N-aryl-benzimidazole)benzene compound. In one embodiment, the layer is an electron transport layer.

In one embodiment, at least one of the tris(N-aryl-benzimidazole)benzene compounds is included in a charge transport layer, for example, an electron transport layer of an electronic device.

In one embodiment, compositions are provided comprising the above-described compounds and at least one solvent, processing aid, charge transporting material, or charge blocking material. These compositions can be in any form, including, but not limited to solvents, emulsions, and colloidal dispersions.

In one embodiment, a composition comprising at least one tris(N-aryl-benzimidazole)benzene compound and at least one of a solvent, a process aid, and a polymer is provided. In one embodiment, the composition comprises a conductive polymer.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Illustrative Electronic Devices, and finally Examples.

Definitions and Clarification of Terms

Before addressing details of embodiments described below, some terms are defined or clarified.

As used herein, the term "alkyl" includes both branched and straight-chain saturated aliphatic hydrocarbon groups having the specified number of carbon atoms. Unless otherwise indicated, the term is also intended to include cyclic groups. Examples of alkyl groups include methyl, ethyl, propyl, isopropyl, isobutyl, secbutyl, tertbutyl, pentyl, isopentyl cyclopentyl, hexyl, cyclohexyl, isohexyl and the like. The term "alkyl" further includes both substituted and unsubstituted hydrocarbon groups. In some embodiments, the alkyl group may be mono-, di- and tri-substituted. One example of a substituted alkyl group is trifluoromethyl. Other substituted alkyl groups are formed from one or more of the substituents described herein. In one embodiment, alkyl groups have 1 to 12 carbon atoms. In other embodiments, the group has 1 to 6 carbon atoms.

The term "aryl" means an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. In some embodiments, aryl groups have 6 to 20 carbon atoms.

The term "heteroaryl," as used herein, refers to a 5 to 10 membered monocyclic or bicyclic carbon containing aromatic ring having 1 to 3 of its ring members independently selected from nitrogen, sulfur or oxygen. In some embodiments, monocyclic rings have 5 to 6 members. In certain embodiments, bicyclic rings have 8 to 10 membered ring structures. The heteroaryl group may be unsubstituted or substituted. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, and quinazolinyl.

The term "aryl-alkyl-aryl" refers to a group —Ar"—R"—Ar"— where Ar" is aryl and R" is alkyl as described herein.

The prefix "fluoro" indicates that one or more hydrogen atoms has been replaced with a fluorine atom.

The prefix "thio" indicates that one or more oxygen atoms has been replaced with a sulfur atom.

The term "halogen" includes fluorine, chlorine, iodine, and bromine.

The term "alkoxy," as used herein, refers to the group R—O— where R is an alkyl. In some embodiments, the alkyl has 1 to 4 carbon atoms.

The term "aryloxy," as used herein, refers to the group Ar—O—, where Ar is an aryl group.

As used herein, the term "heteroaryloxy" refers to a group —O—$Ar^H$ where $Ar^H$ is a heteroaryl group as defined herein.

The term "alkenyl" refers to an unsaturated or partially unsaturated aliphatic hydrocarbon group having the specified number of carbon atoms, for example ethenyl, 1-propenyl, 2-butenyl, etc. The term "alkenyl" further includes both unsubstituted and mono-, di- and tri-substituted hydrocarbon groups. Some alkenyl groups have 2 to 7 carbon atoms.

The term "cycloalkyl" includes cyclized alkyl chains having the specified number of carbon atoms, e.g., cyclopropyl, cyclobutyl, cyclopentyl, and cyclohexyl. In some embodiments, cycloalkyl groups have 3 to 8 carbon atoms.

The term "arylalkyl" means aryl-alkyl- wherein the aryl portion, as herein before defined, is suitably substituted on any open ring position with an alkyl moiety wherein the alkyl chain is either a ($C_1$-$C_6$) straight or ($C_3$-$C_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "alkoxycarbonyl" refers to a —$CO_2R^9$ group where $R^9$ is alkyl or aryl.

Unless otherwise indicated, all groups can be substituted or unsubstituted.

An optionally substituted group, such as, but not limited to, alkyl, aryl, or heteroalkyl, may be substituted with one or more substituents which may be the same or different. Suitable substituents include alkyl, aryl, nitro, cyano, $-N(R^7)(R^8)$, halo, hydroxy, carboxy, alkenyl, alkynyl, cycloalkyl, heteroaryl, alkoxy, aryloxy, heteroaryloxy, alkoxycarbonyl, perfluoroalkyl, perfluoroalkoxy, arylalkyl, thioalkoxy, $-S(O)_2-N(R^7)(R^8)$, $-C(=O)-N(R^7)(R^8)$, $(R^7)(R^8)$N-alkyl, $(R^7)(R^8)$N-alkoxyalkyl, $(R^7)(R^8)$N-alkylaryloxyalkyl, $-S(O)_s-$ aryl (where s=0-2) or $-S(O)_s-$heteroaryl (where s=0-2). Each $R^7$ and $R^8$ is independently an optionally substituted alkyl, cylcoalkyl, or aryl group. $R^7$ and $R^8$, together with the nitrogen atom to which they are bound, can form a ring system in certain embodiments.

The prefix "hetero" indicates that one or more carbon atoms has been replaced with a different atom.

The term "group" is intended to mean a part of a compound, such as a substituent in an organic compound.

The term "monomer" refers to a compound capable of being polymerized. The term "monomeric unit" refers to units which are repeated in a polymer.

The term "polymeric" is intended to encompass oligomeric species and include materials having 2 or more monomeric units.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms which are joined by a bond).

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photo switches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

As used herein, the term "photoactive" refers to a material that emits light when activated by an applied voltage (such as in a light-emitting diode or light-emitting electrochemical cell), or responds to radiant energy and generates a signal with or without an applied bias voltage (such as in a photodetector). An example of a photoactive layer is an emitter layer.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the term "charge transport," when referring to a layer or material is intended to mean such layer or material facilitates migration of such charge through the thickness of such layer, material, member, or structure with relative efficiency and small loss of charge, and is meant to be broad enough to include materials that may act as a hole transport or an electron transport material. The term "electron transport" when referring to a layer or material means such a layer or material, member or structure that promotes or facilitates migration of electrons through such a layer or material into another layer, material, member or structure.

The term "charge blocking," when referring to a layer, material, member, or structure, is intended to mean such layer, material, member or structure reduces the likelihood that a charge migrates into another layer, material, member or structure. The term "electron blocking" when referring to a layer, material, member or structure is intended to mean such layer, material, member or structure that reduces that likelihood that electrons migrate into another layer, material, member or structure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The use of "a" or "an" are employed to describe elements and components of the invention. This is done merely for convenience and to give a general sense of the invention. This description should be read to include one or at least one and the singular also includes the plural unless it is obvious that it is meant otherwise.

Group numbers corresponding to columns within the Periodic Table of the elements use the "New Notation" convention as seen in the CRC Handbook of Chemistry and Physics, 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

Illustrative Uses

Organic electronic devices that may benefit from having one or more layers comprising at least one benizimidazole compound include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode). Other uses for the compositions include coating materials for memory storage devices, antistatic films, biosensors, electrochromic devices, solid electrolyte capacitors, energy storage devices such as a rechargeable battery, and electromagnetic shielding applications.

Referring to FIG. 1, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8, 10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer,* Nature 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 (4$^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4, 4'-diamine (TPD), 1,1 bis[(di-4-tolylamino) phenyl]cyclohexane (TAPC), N,N'bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino)styryl]-5-[p-(diethylamino)phenyl] pyrazoline (PPR or DEASP), 1,2 trans-bis (9H-carbazol-9-yl)cyclobutane (DCZB), N,N,N',N'tetrakis (4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly (phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or band-gap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

EXAMPLES

The concepts described herein will be further described in the following examples, which do not limit the scope of the invention described in the claims.

Example 1

Example 1 demonstrates the preparation of 2,2',2"-(1,3,5-Phenylene)-tris[1-phenyl-1H-benzimidazole]

N-phenyl-1,2-phenylenediamine (0.541 mol) was combined with 1,3,5-benzene-tricarbonyl chloride (0.181 mol) in 1.8 L N-methylpyrrolidone (NMP) and stirred for 2 hrs at room temperature and then heated to 50° C. overnight. The reaction mixture was cooled to room temperature and precipitated into water (5 parts water to 1 part reaction mixture) and filtered through a medium frit then dried in a vacuum oven. Approx. 138 g of dried solid material was combined with POCl3 (0.5 kg) and carefully warmed to 98° C. for 14 hrs. The mixture was cooled to room temperature, then precipitated into stirred ice chips and water (5 parts ice and one part reaction mixture). The quenched material was neutralized with 50% NaOH to pH 9, filtered through a medium frit, and then dried in a vacuum oven. The solid was dissolved in dichloromethane (DCM), eluted through a silica plug and then purified by silica column chromatography using ethyl acetate/hexanes. 58.51 g of solid were isolated by concentrating the eluant almost to dryness, then filtering followed by drying with vacuum. The average yield for each of the two steps was 70%.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A method for preparing a compound of Formula I:

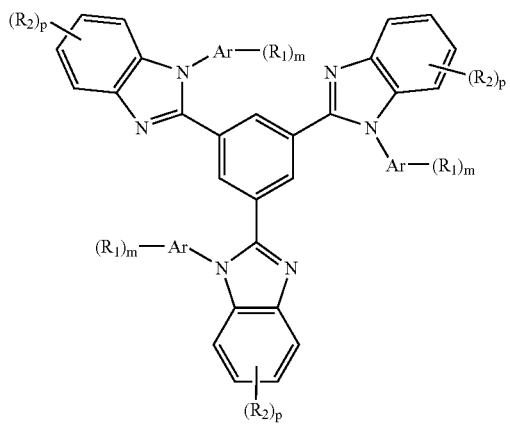

Formula I said method comprising the steps of:
contacting a compound of Formula II:

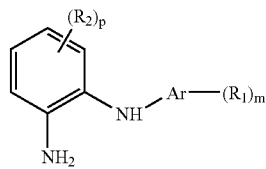

Formula II with 1,3,5-benzene-tricarbonyl chloride in the presence of a polar aprotic solvent to form an amide adduct; and subsequently condensing the amide with a proximate anilino group present in the adduct in the presence of a condensing agent wherein the condensing agent is $POCl_3$, diphenyl chlorophosphate or a combination thereof to form a compound of Formula I wherein:

$R_1$ is the same or different at each occurrence and is hydrogen, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

$R_2$ is the same or different at each occurrence and is hydrogen, $C_1$-$C_{20}$ alkyl, halo, $C_1$-$C_{20}$ fluoroalkyl, $C_6$-$C_{20}$ aryl, $C_4$-$C_{20}$ heteroaryl, $C_1$-$C_{20}$ alkoxy, $C_6$-$C_{20}$ aryloxy, $C_1$-$C_{20}$ thioalkoxy, $C_6$-$C_{20}$ thioaryloxy, amino, carboxyl, cyano, nitro, or two adjacent R groups together can be —O—$(CH_2)_t$—O— or a fused aromatic ring;

Ar is the same or different at each occurrence and is $C_6$-$C_{20}$ aryl or $C_4$-$C_{20}$ heteroaryl;

m and p are the same or different at each occurrence and are each independently 0 or an integer from 1 to 3; and t is the same or different at each occurrence and is an integer from 1 to 6.

2. The method of claim 1 wherein 2,2',2''-(1,3,5-Phenylene)-tris[1-phenyl-1H-benzimidazole] is prepared by contacting N-phenyl-1,2-phenylenediamine with 1,3,5-benzene-tricarbonyl chloride.

3. The method of claim 1 wherein condensing the amide with a proximate anilino group present in the adduct in the presence of the condensing agent is performed at a temperature of from about 25° C. to about 150° C. for about 1 to about 24 hours.

4. The method of claim 1 wherein the condensing agent is $POCl_3$.

5. The method of claim 1 wherein the polar aprotic solvent is N-Methyl-2-Pyrrolidone (NMP); dimethylformamide (DMF); dimethylacetamide (DMAC); dioxane, tetrahydrofuran (THF); dimethyl sulfoxide (DMSO); toluene; dichlorobenzene; dichloromethane; dichloroethane; or combinations thereof.

6. The method of claim 5 wherein the polar aprotic solvent is N-Methyl-2-Pyrrolidone (NMP).

7. The method of claim 1 further comprising isolating the adduct before contact with the condensing agent.

8. The method of claim 7 wherein the adduct is isolated by cooling to room temperature, precipitating into $NaHCO_3$, and washing with water.

9. The method of claim 1 further comprising isolating the compound of Formula I from the mixture.

10. The method of claim 9 wherein the compound is isolated by cooling the mixture to room temperature, precipitating the compound into ice water, neutralizing with a strong base, and collecting by filtration.

* * * * *